(12) United States Patent
Smith et al.

(10) Patent No.: US 8,119,840 B2
(45) Date of Patent: Feb. 21, 2012

(54) ETHAMBUTOL BASED NITRIC OXIDE DONORS

(75) Inventors: Daniel J. Smith, Stow, OH (US); Marcos Lopez, Wauwatosa, WI (US)

(73) Assignee: The University of Akron, Akron, OH (US)

( * ) Notice: Subject to any disclaimer, the term of this patent is extended or adjusted under 35 U.S.C. 154(b) by 856 days.

(21) Appl. No.: 11/817,377

(22) PCT Filed: Mar. 3, 2006

(86) PCT No.: PCT/US2006/007774
§ 371 (c)(1),
(2), (4) Date: May 19, 2008

(87) PCT Pub. No.: WO2006/096572
PCT Pub. Date: Sep. 14, 2006

(65) Prior Publication Data
US 2009/0069449 A1    Mar. 12, 2009

Related U.S. Application Data

(60) Provisional application No. 60/658,648, filed on Mar. 4, 2005.

(51) Int. Cl.
*C07C 243/02* (2006.01)
*B05D 1/00* (2006.01)
*A61F 13/00* (2006.01)

(52) U.S. Cl. ............ 564/113; 264/484; 514/772.4; 525/376; 534/552

(58) Field of Classification Search ............ 564/113; 514/772.4; 534/552; 525/376; 264/484
See application file for complete search history.

(56) References Cited

U.S. PATENT DOCUMENTS

| | | |
|---|---|---|
| 4,043,331 A | 8/1977 | Martin et al. |
| 4,878,908 A | 11/1989 | Martin et al. |
| 5,039,705 A | 8/1991 | Keefer et al. |
| 5,519,020 A | 5/1996 | Smith et al. |
| 5,770,645 A | 6/1998 | Stamler et al. |
| 6,382,526 B1 | 5/2002 | Reneker et al. |
| 6,520,425 B1 | 2/2003 | Reneker |
| 6,695,992 B2 | 2/2004 | Reneker |
| 6,753,454 B1 | 6/2004 | Smith et al. |

OTHER PUBLICATIONS

Wilkinson, R. G., et al., J. Med. Chem., 5, 835-845 (1962).

*Primary Examiner* — Shailendra Kumar
(74) *Attorney, Agent, or Firm* — Renner Kenner Greive Bobak Taylor & Weber

(57) ABSTRACT

The present invention relates generally to nitric oxide releasing pharmaceutical compounds. More particularly, the present invention relates to pharmaceutical compositions that release nitric oxide under physiological conditions. In one embodiment, the present invention relates to new chemical compounds—diazeniumdiolates nitric oxide donors—that are based on ethambutol possessing physiological and biomedical activity.

24 Claims, 2 Drawing Sheets

ETHAMBUTOL BASED NITRIC OXIDE DONORS

This application is a 371 of PCT/US06/07774, filed Mar. 3, 2006.

FIELD OF THE INVENTION

The present invention relates generally to nitric oxide releasing pharmaceutical compounds. More particularly, the present invention relates to pharmaceutical compositions that release nitric oxide under physiological conditions. In one embodiment, the present invention relates to new chemical compounds—diazeniumdiolates nitric oxide donors—that are based on ethambutol possessing physiological and biomedical activity.

BACKGROUND OF THE INVENTION

Recent research has discovered the ubiquitous synthesis and use of nitric oxide (NO) throughout the biological systems of animals. For example, NO has been found to play a role in blood pressure regulation, blood clotting, neurotransmission, smooth muscle relaxation, and immune systems. For example, within the immune system, NO is believed both to inhibit key metabolic pathways, thereby inhibiting tumor growth, and to serve as an outright toxin that can be used to kill cells.

Furthermore, NO has been found to be a potent vasodilator within the bronchial circulation system of the lungs and is believed to play an important role in regulating pulmonary circulation. Nitric oxide is also believed to relax the muscles within lung airways, thereby regulating breathing.

Thus, it is believed that the insufficient production of NO within various biological functions results in deleterious effects as manifested in various immune deficiencies, asthma, bacterial infections, impotence, and high blood pressure, to name a few. From a pharmacological standpoint, the delivery of NO to the body may serve as a remedy for ailments caused by the insufficient production of NO within the body.

Nitric oxide, however, as it is used within the enumerable biological functions of animals, is highly controlled and regulated because excess amounts of NO can be hazardous to living animals. For example, the introduction of NO into the blood stream can cause the irreversible lowering of blood pressure, ultimately leading to death. Thus, the introduction of NO into the body is not the simple solution to the effects caused by insufficient NO production within the body.

There are known pharmaceutical compositions capable of delivering NO. Namely, Keeffer et al, U.S. Pat. No. 5,039,705, discloses pharmaceutical compositions of the formula

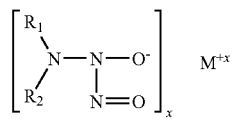

wherein $R_1$ and $R_2$ are independently chosen from straight chain and branched chain alkyl groups of 1 to 12 carbon atoms or benzyl, with the proviso that no branch occur on the alpha carbon of the alkyl groups, or $R_1$ and $R_2$ together with the nitrogen atom they are bonded to form a pyrrolidino, piperidino, piperazino or morpholino ring, $M^{+x}$ is a pharmaceutically acceptable cation, wherein x is the valence of the cation. Because this particular compound is a salt, the preferred method of administering this compound to animals is through injection into the bloodstream. It is also noteworthy that this particular compound is highly soluble in biological fluids thereby quickly releasing the NO which is loaded to the molecule.

Also, Keeffer et al., U.S. Pat. No. 5,366,997, discloses a similar pharmaceutical composition of the formula

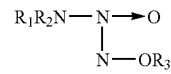

wherein $R_1$ and $R_2$ are independently chosen from $C_1$ to $C_{12}$ straight chain alkyl, $C_1$ to $C_{12}$ alkoxy or acyloxy substituted straight chain alkyl, $C_2$ to $C_{12}$ hydroxy or halo substituted straight chain alkyl, $C_3$ to $C_{12}$ branched chain alkyl, $C_3$ to $C_{12}$ hydroxy, halo, alkoxy, or acyloxy substituted branched chain alkyl, $C_3$ to $C_{12}$ straight olefinic and $C_3$ to $C_{12}$ branched chain olefinic which are unsubstituted or substituted with hydroxy, alkoxy, acyloxy, halo or benzyl. In another embodiment, $R_1$ and $R_2$ can also comprise various heterocyclic ring molecules as described therein.

It should be appreciated that the molecules as described by Keeffer at al are soluble within body fluids. Chemistry dictates as much, as does the disclosure of Keeffer et al as it is recommended to administer these drugs intravenously. It should further be appreciated that upon the intravenous introduction of these chemicals to a living animal, NO will be introduced throughout the body as the soluble compound disseminates throughout the body. As discussed above, unwarranted or overexposure of NO can have many harmful effects on living animals.

The importance of nitric oxide (NO) in biological repair mechanisms is well known even though the precise mechanism of its action has not been completely elucidated. Nitric oxide is known to inhibit the aggregation of platelets and to reduce smooth muscle proliferation, which is known to reduce restenosis. When delivered directly to a particular site, it has been shown to prevent or reduce inflammation at the site where medical personnel have introduced foreign objects or devices into the patient.

Researchers have sought various ways to deliver NO to damaged tissue and to tissues and organs at risk of injury. Nitric oxide can be delivered systemically, but such delivery can bring undesired side effects with it. Ideally, NO should be delivered in a controlled manner specifically to those tissues and organs that have been injured or are at risk of injury. Various compounds have been used to deliver NO therapeutically. Diazeniumdiolates (NONOates) exhibit the ability to release NO in the presence of a proton donor. Other classes of NO donors either require enzymatic activation to release therapeutic levels of nitric oxide, or they release both NO and undesired free radicals.

For purposes of this disclosure, those amine molecules that have been reacted with NO will be referred to as having NO loaded thereto. Heretofore in the art, those amine molecules having NO loaded thereto have been referred to as NONOates. Thus, the NO donor molecules of the present invention are NONOates.

The use of NONOates for the release of nitric oxide to specifically treat tissue that has been injured or is at risk of injury during sepsis or shock has been described in at least Saavedra et al., U.S. Pat. No. 5,814,656, the disclosure of which is incorporated herein by reference. Insoluble polymeric NONOates have also been generally described in Smith et al, U.S. Pat. No. 5,519,020, the disclosure of which is also incorporated herein by reference. These polymers were used to deliver NO to specific tissues, and results have shown that controlled release of NO to a specific site greatly reduced the inflammation and accelerates the healing process at that site. However, heretofore, these compositions have had to be delivered either by topical application or by coating onto the medical device. While such applications have been successful, the need continues to exist to provide a manner in which the NONOate compositions could be exposed to a greater surface area of the medical devices to which they are applied. The use of NONOates as coatings on implantable medical devices is also disclosed in Stemler et al., U.S. Pat. No. 5,770,645, the disclosure of which is also incorporated herein by reference.

In addition to the need set forth hereinabove, the process of coating some medical devices, particularly implantable devices, may have adverse effects on and alter the physical properties of the device. This can contribute to serious complications from the body's own defense to the medical device as foreign material.

The technique of electrostatic spinning, also known within the fiber forming industry as electrospinning, of liquids and/or solutions capable of forming fibers, is well known and has been described in a number of patents as well as in the general literature. The process of electrostatic spinning generally involves the introduction of a liquid into an electric field, so that the liquid is caused to produce fibers. These fibers are generally drawn to a cathode for collection. During the drawing of the liquid, the fibers harden and/or dry. This may be caused by cooling of the liquid, i.e., where the liquid is normally a solid at room temperature; by evaporation of a solvent, e.g., by dehydration (physically induced hardening); or by a curing mechanism (chemically induced hardening).

Previously known NONOates, however, are soluble in physiological mediums, and thus disseminate throughout the body once introduced therein. NONOates, which are insoluble in physiological mediums, upon introduction into the body, will not rapidly be distributed throughout the body allowing for the site specific delivery of NO, and are thus very desirable. Thus, there is a need in the art for a NO generating compound or compounds that are insoluble in physiological mediums. Physiological mediums will refer to those environments found within the bodies of animals, particularly humans, and include aqueous mediums.

SUMMARY OF THE INVENTION

The present invention relates generally to nitric oxide releasing pharmaceutical compounds. More particularly, the present invention relates to pharmaceutical compositions that release nitric oxide under physiological conditions. In one embodiment, the present invention relates to new chemical compounds—diazeniumdiolates nitric oxide donors—that are based on ethambutol possessing physiological and biomedical activity. This present invention provides a new class of compounds for the treatment of cardiovascular abnormalities and to serve as antibiotics.

In one embodiment, the present invention relates to a compound represented by the following formula:

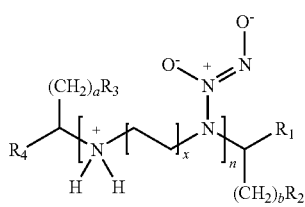

wherein x, n, a, and b can all be selected independently from one another, and x is an integer from 2 to about 20; n is an integer from 1 to about 20, and a and b are independently integers from 1 to about 10; and wherein $R_1$, $R_2$, $R_3$ and $R_4$ are independently selected from H, alkyl groups, alkylene groups, alcohol groups, halides, nitrile groups, nitro groups, thiol groups, carboxylic groups, ketone groups, acyl halide groups, anhydride groups, amide groups, cyclo groups, biclyco groups, benzyl groups, polycyclo groups, or heteroclyco groups.

In another embodiment, the present invention relates to a process for the production of fibers of linear poly(ethylenimine) modified with a compound according to the following formula:

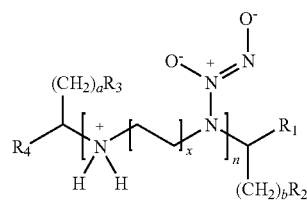

wherein x, n, a, and b can all be selected independently from one another, and x is an integer from 2 to about 20; n is an integer from 1 to about 20, and a and b are independently integers from 1 to about 10; wherein $R_1$, $R_2$, $R_3$ and $R_4$ are independently selected from H, alkyl groups, alkylene groups, alcohol groups, halides, nitrile groups, nitro groups, thiol groups, carboxylic groups, ketone groups, acyl halide groups, anhydride groups, amide groups, cyclo groups, biclyco groups, benzyl groups, polycyclo groups, or heteroclyco groups, and wherein the compound can yield, produce and/or generate nitric oxide.

In still another embodiment, the present invention relates to a compound represented by the following formula:

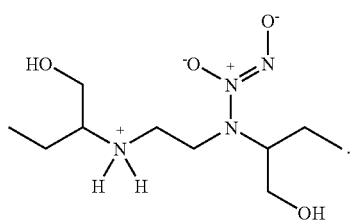

DETAILED DESCRIPTION OF THE INVENTION

Figure 1:
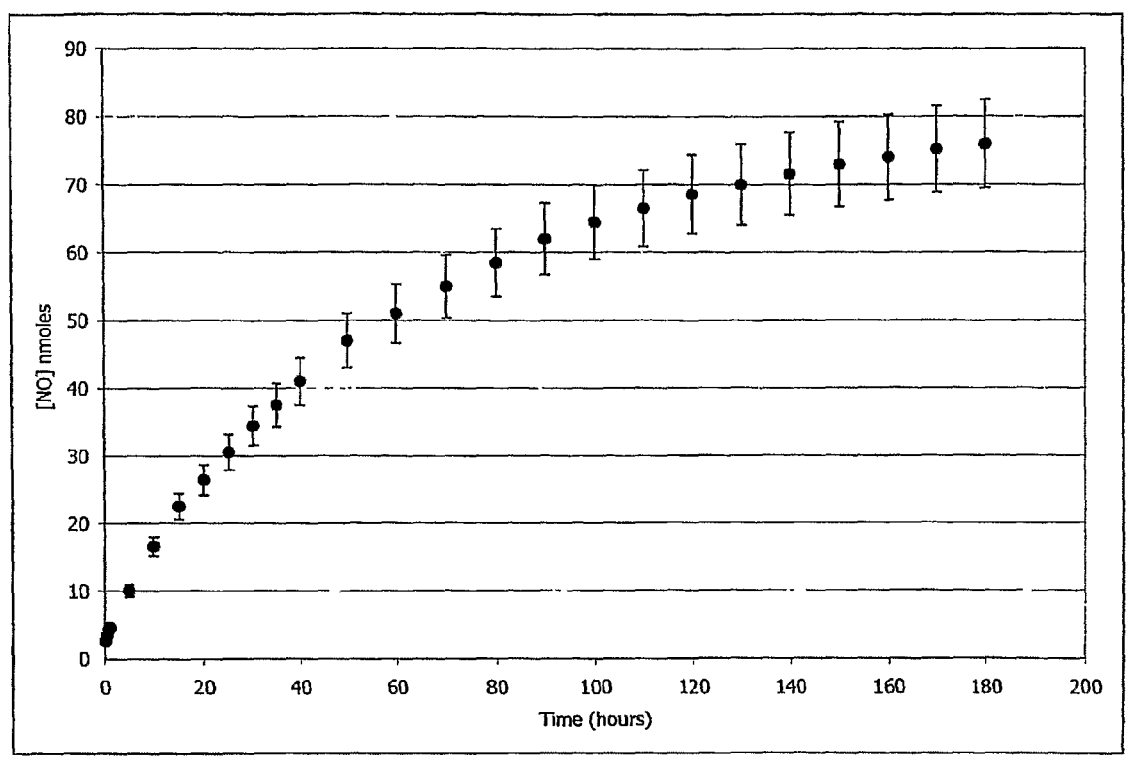
FIG. 1 is a plot of nitric oxide release from ethambutol diazeniumdiolate at 37° C. and a pH of 7.4.
Figure 2:
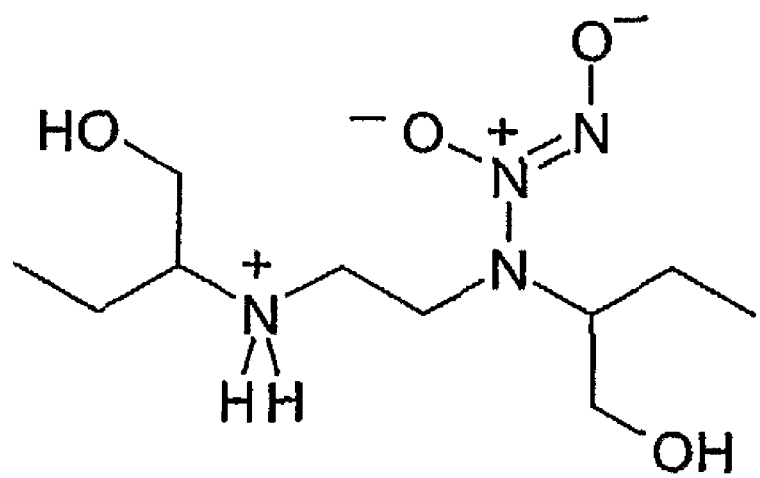
FIG. 2 is a drawing of ethambutol diazeniumdiolate.
Figure 3:
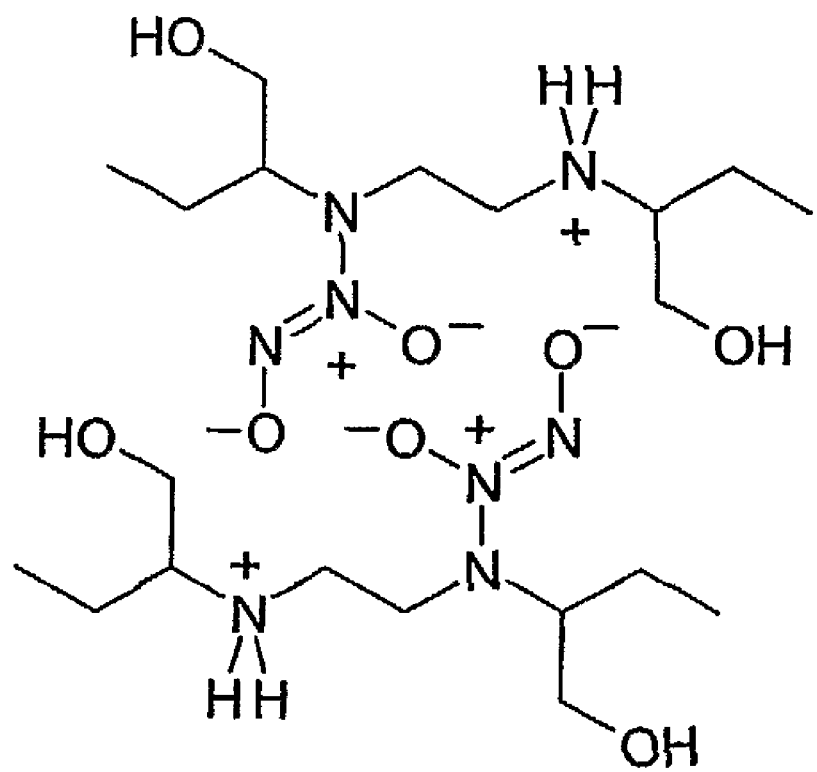
FIG. 3 is a drawing of ethambutol diazeniumdiolate dimer.

The present invention relates generally to nitric oxide releasing pharmaceutical compounds. More particularly, the present invention relates to pharmaceutical compositions that release nitric oxide under physiological conditions. In one embodiment, the present invention relates to new chemical compounds—diazeniumdiolates nitric oxide donors—that are based on ethambutol possessing physiological and biomedical activity. This present invention provides a new class of compounds for the treatment of cardiovascular abnormalities and to serve as antibiotics.

In another embodiment, the present invention relates to the production of fibers and/or nanofibers of linear poly(ethylenimine) that contain, are coated with and/or are modified with nitric oxide (NO). For the remainder of the specification and claims when the phrase "NO-modified linear poly(ethylenimine fibers and/or nanofibers" is used, this phrase shall include linear poly(ethylenimine fibers and/or nanofibers that contain, are coated with and/or are modified with nitric oxide (NO), as is discussed above.

More particularly, in this instance, the present invention relates to the use of these NO-modified linear poly(ethylenimine) fibers and/or nanofibers that can be applied to medical devices such as catheters, stents, vascular grafts, wound dressings, and the like, to release therapeutic levels of NO for wound healing or other medical purposes. In still another embodiment, the present invention relates to the production of electrospun nanofibers of linear poly(ethylenimine) diazeniumdiolate for use in the delivery of NO to a patient.

The fibers and/or nanofibers of the present invention can be fabricated according to a variety of methods known in the art including, but not limited to, electrospinning, wet spinning, dry spinning, melt spinning, and gel spinning. Electrospinning is particularly suitable for fabricating the fibers and/or nanofibers of the present invention inasmuch as it tends to produce the thinnest (i.e., finest denier) fibers of any of the foregoing methods. Electrospinning techniques are described in U.S. Pat. Nos. 4,043,331; 4,878,908; and 6,753,454, which are hereby incorporated by reference in their entireties.

Another particularly effective method for producing the fibers and/or nanofibers of the present invention comprises the nanofibers by gas jet method (i.e., NGJ method). This method has been previously described and is known in the art. Briefly, the method comprises using a device having an inner tube and a coaxial outer tube with a sidearm. The inner tube is recessed from the edge of the outer tube thus creating a thin film-forming region. Polymer melt is fed in through the sidearm and fills the empty space between the inner tube and the outer tube. The polymer melt continues to flow toward the effluent end of the inner tube until it contacts the effluent gas jet. The gas jet impinging on the melt surface creates a thin film of polymer melt, which travels to the effluent end of tube where it is ejected forming a turbulent cloud of nanofibers.

Exemplary patents that disclose NGJ methods include U.S. Pat. Nos. 6,753,454; 6,695,992; 6,520,425; and 6,382,526, all of which are incorporated by reference in their entireties.

Both electrospinning and NGJ techniques permit the processing of polymers from both organic and aqueous solvents. Furthermore, based on the present invention, these techniques permit the incorporation, dispersion (both homogeneous and heterogeneous dispersions), and/or localized dispersion of discrete particles and/or soluble non-fiber forming additives into the resulting fibers via the spinning/gas jet fluid.

In one embodiment, the diameter of the fibers and/or nanofibers utilized and/or contained in the present invention ranges from about 1 nanometer to about 20,000 nanometers, or from about 10 nanometers to about 10,000 nanometers, or from about 20 nanometers to about 5,000 nanometers, or from about 30 nanometers to about 2,500 nanometers, or from about 40 nanometers to about 1,000 nanometers, or from about 50 nanometers to about 500 nanometers, or even from about 60 nanometers to about 250 nanometers. In another embodiment, the fibers used in the present invention are electrospun fibers having diameters within the range of about 3 nanometers to about 3000 nanometers, of from about 10 nanometers to about 500 nanometers, or even from about 25 nanometers to about 100 nanometers. Here, as well as elsewhere in the specification and claims, different range limits may be combined.

The length of the fibers contained in the present invention is not critical. Any length fibers can be used. Suitable fiber lengths include, but are not limited to, fibers of at least about 1 centimeter in length, fibers of at least about 10 centimeters in length, fibers of at least about 50 centimeters in length, fibers of at least about 1 meter in length, fibers of at least about 5 meters in length, fibers of at least about 25 meters in length, fibers of at least about 50 meters in length, fibers of at least about 100 meters in length, fibers of at least about 250 meters in length, fibers of at least about 500 meters in length, fibers of at least about 1 kilometer in length, and even fibers of at least about 5 kilometers in length. Again, here, as well as elsewhere in the specification and claims, different range limits may be combined.

Turning to the nitric oxide aspect of the present invention, the structures of the compounds according to this invention are represented by the following general formula:

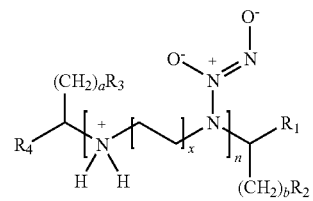

wherein x, n, a, and b can all be selected independently from one another, and x is an integer from 2 to about 20; n is an integer from 1 to about 20, and a and b are independently integers from 1 to about 10. In another embodiment, x is an integer from 2 to about 15; n is an integer from 1 to about 15, and a and b are independently integers from 1 to about 8. In still another embodiment, x is an integer from 2 to about 10; n is an integer from 1 to about 10, and a and b are independently integers from 1 to about 4. In yet another embodiment, each of the above ranges for x, n, a, and b include every integer therein and such integers can be used as limits for additional ranges. Here, as well as elsewhere in the specification and claims, range limits can be combined.

$R_1$, $R_2$, $R_3$ and $R_4$ can be selected independently of one another and can be any functional group or combination thereof. Such atoms/groups include, but not limited to, H, alkyl groups, alkylene groups, alcohol group, halides, nitrile groups, nitro groups, thiol groups, carboxylic groups, ketone groups, acyl halide groups, anhydride groups, amide groups, cyclo groups, biclyco groups, benzyl groups, polycyclo groups, and heteroclyco groups.

In another embodiment, $R_1$, $R_2$, $R_3$ and $R_4$ can be any functional group or combination thereof selected from $C_1$ to about $C_{20}$ alkyl groups, $C_2$ to about $C_{20}$ alkylene groups, alcohol group, halides, nitrile groups, nitro groups, thiol groups, carboxylic groups, $C_3$ to about $C_{20}$ ketone groups, acyl halide groups, anhydride groups, amide groups, $C_3$ to about $C_{10}$ cyclo groups, $C_6$ to about $C_{20}$ biclyco groups, benzyl groups, polycyclo groups, and heteroclyco groups. In still another embodiment, $R_1$, $R_2$, $R_3$ and $R_4$ can be any functional group or combination thereof selected from $C_1$ to about $C_{10}$ alkyl groups, $C_2$ to about $C_{10}$ alkylene groups, alcohol group, halides, nitrile groups, nitro groups, thiol groups, carboxylic groups, $C_3$ to about $C_{10}$ ketone groups, acyl halide groups, anhydride groups, amide groups, $C_3$ to about $C_8$ cyclo groups, $C_6$ to about $C_{16}$ biclyco groups, benzyl groups, polycyclo groups, and heteroclyco groups. In still another embodiment, $R_1$, and $R_4$ are ethyl groups and $R_2$ and $R_3$ are OH groups. Here, as well as elsewhere in the specification and claims, range limits can be combined.

Example 1

Preparation of Ethambutol Free Base

Ethambutol Dihydrochloride (ETB) is obtained from MP Biomedicals (Aurora, Ohio). ETB (7 grams) are dissolved in 100 mL of a saturated solution of sodium carbonate in 5M NaOH. The solution is stirred for 10 minutes and the free based ETB is extracted with three volumes of chloroform. The solution is dried over sodium sulfate. After filtration, the chloroform is removed by rotary evaporation. Ethambutol is represented in the structure below (a).

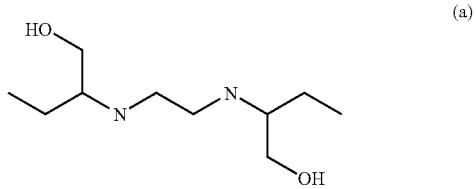

(a)

Example 2

Preparation of 2-2'-(Ethylenediimino)-di-1-ethanol dihydrochloride (ETE)

The preparation of this compound is done according to the method described in a publication by R. G. Wilkinson, M. B. Centrall and R. G. Shepherd. J. Med. Chem., 5, 835-845 (1962). Briefly, 2-aminoethanol (0.1 mole) and ethylene bromide (0.01 mole) are heated at 100 to 115° C. in an oil bath for 25 minutes. After cooling, 0.02 mole of KOH in 10 ml of hot ethanol are added. The precipitated salt is removed by filtration. The filtrate is washed with 10 ml of acetone-ethanol (1:1) to remove trace KBr. To the filtrate, 8 ml of 7.8 N ethanolic HCl are added, and after cooling to −5° C. for 0.5 hrs, white crystals are obtained. The product is further recrystallized with 45 mL of hot ethanol. ETE is represented in the structure below (b). The free base is formed in a manner similar to that which is described in Example 1 above. Specifically, a quantity of ETE is dissolved in a saturated solution of sodium carbonate in 5M NaOH. The solution is stirred and the ETE free base is extracted with three volumes of chloroform. The solution is dried over sodium sulfate. After filtration, the chloroform is removed by rotary evaporation.

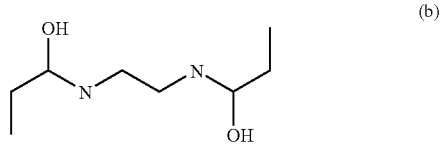

(b)

Nitric Oxide Modification of the Molecules Synthesized in Examples:

The polyamine derivatives synthesized above are modified with nitric oxide to form the corresponding NONOates. About 1 to about 5 grams of each of the polyamine derivatives synthesized above are dissolved in 80 ml of chloroform in a high pressure bottle equipped with a magnetic stir bar. The stirred mixture is purged with nitrogen gas and then purged with NO gas. The mixture is then brought to 70 psi of NO and left to react for 24 hours under continuous stirring. The reaction is purged with nitrogen gas and an aliquot was removed for UV analysis at 240 nm. The reaction is repeated until a maximum UV absorbance is achieved, which is indicative of complete NO loading to the polyamine derivative molecules. The NO gas is released, and the mixture is purged and flushed with nitrogen. The solvent is removed by rotary evaporation at room temperature followed by four hours in a vacuum oven set at room temperature. The sample containers are flushed with nitrogen gas and stored at −20° C. in a desiccator.

Nitric Oxide Release Profiles:

The nitric oxide release from the above synthesized NONOates is measured using a Siemens Nitric Oxide Analyzer 280A. The analyzer is connected to a release chamber consisting of an impinger bottle that had a one-way TEFLON® stop cock valve attached in order to prevent the escape of any generated nitric oxide. TEFLON® flow meters are inserted at the beginning of the circuit just before entry into the analyzer, and a helium tank with regulator is connected to the first flow meter.

The release profile is performed by adding about 10 mg of the NO donor molecules prepared above to 4 ml of phosphate-buffered saline (PBS) (pH 7.4) in an impinger bottle that is subjected to continuous stirring. The amount of liberated NO is determined by regularly flushing helium through the solution and into the analyzer. Typically, measurements are taken every 2 to 4 hours during the first 18 hours and then every 12 hours thereafter. Eventually, readings only need to be taken every 24 hours as the end of the release profile is approached. Helium gas is flushed through the system at 12 psig and the first flow meter is set to 150 ml/min. The second flow meter is adjusted to allow maximum flow. The release data is then used to compile the release profiles. The release profiles of ETBD as represented in FIG. 1 depict NO release from the ETB NONOate in nmol NO/mg NONOate versus time in hours.

Although the invention has been described in detail with particular reference to certain embodiments detailed herein, other embodiments can achieve the same results. Variations and modifications of the present invention will be obvious to those skilled in the art, and the present invention is intended to cover in the appended claims all such modifications and equivalents.

What is claimed is:

1. A compound represented by the following formula:

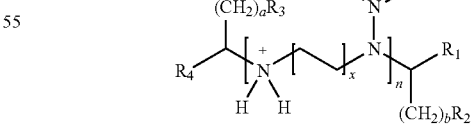

wherein x, n, a, and b can all be selected independently from one another, and x is an integer from 2 to about 20; n is an integer from 1 to about 20, and a and b are independently integers from 1 to about 10; and wherein $R_1$, $R_2$, $R_3$ and $R_4$ are independently selected from H, alkyl groups, alkylene groups, alcohol groups, halides, nitrile groups, nitro groups, thiol groups, carboxylic groups, ketone groups, acyl halide groups, anhydride groups, amide groups, cyclo groups, biclyco groups, benzyl groups, polycyclo groups, or heteroclyco groups.

2. The compound of claim 1, wherein x is an integer from 2 to about 15.

3. The compound of claim 1, wherein x is an integer from 2 to about 10.

4. The compound of claim 1, wherein n is an integer from 1 to about 15.

5. The compound of claim 1, wherein n is an integer from 1 to about 10.

6. The compound of claim 1, wherein a and b are independently integers from 1 to about 8.

7. The compound of claim 1, wherein a and b are independently integers from 1 to about 4.

8. The compound of claim 1, wherein $R_1$, and $R_4$ are ethyl groups.

9. The compound of claim 1, wherein $R_2$ and $R_3$ are OH groups.

10. A process for the production of fibers of linear poly(ethylenimine) modified with a compound according to claim 1, wherein the compound of claim 1 yields nitric oxide.

11. The process of claim 10, wherein the fibers are produced via an electrospinning process.

12. The process of claim 10, wherein the fibers are nanofibers.

13. The process of claim 12, wherein the nanofibers have a diameter in the range of about 1 nanometer to about 20,000 nanometers.

14. The process of claim 12, wherein the nanofibers have a diameter in the range of about 10 nanometers to about 10,000 nanometers.

15. The process of claim 12, wherein the nanofibers have a diameter in the range of about 50 nanometers to about 1,000 nanometers.

16. The process of claim 10, wherein the fibers are produced via an NGJ process.

17. The process of claim 16, wherein the fibers are nanofibers.

18. The process of claim 17, wherein the nanofibers have a diameter in the range of about 1 nanometer to about 20,000 nanometers.

19. The process of claim 17, wherein the nanofibers have a diameter in the range of about 10 nanometers to about 10,000 nanometers.

20. The process of claim 17, wherein the nanofibers have a diameter in the range of about 50 nanometers to about 1,000 nanometers.

21. The process of claim 10, wherein the fibers are used to deliver nitric oxide to a site.

22. The process of claim 21, wherein the delivery site is on or in a patient.

23. The process of claim 10, wherein the fibers are used in or applied to medical devices such as catheters, stents, vascular grafts, and wound dressings, and are designed to release therapeutic levels of nitric oxide for wound healing or other medical purposes based on the inclusion in the fibers of a compound according to claim 1.

24. A compound represented by the following formula:

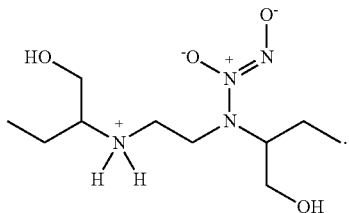

* * * * *